(12) United States Patent
Fukuyama

(10) Patent No.: US 10,422,747 B2
(45) Date of Patent: *Sep. 24, 2019

(54) IMAGING OPTICAL SYSTEM, ILLUMINATION APPARATUS, OBSERVATION APPARATUS, AND WAVEFRONT RECOVERY DEVICE

(71) Applicant: OLYMPUS CORPORATION, Tokyo (JP)

(72) Inventor: Hiroya Fukuyama, Tokyo (JP)

(73) Assignee: Olympus Corporation, Tokyo (JP)

( * ) Notice: Subject to any disclaimer, the term of this patent is extended or adjusted under 35 U.S.C. 154(b) by 323 days.

This patent is subject to a terminal disclaimer.

(21) Appl. No.: 15/408,687

(22) Filed: Jan. 18, 2017

(65) Prior Publication Data

US 2017/0122867 A1    May 4, 2017

Related U.S. Application Data

(63) Continuation of application No. PCT/JP2015/070569, filed on Jul. 17, 2015.

(30) Foreign Application Priority Data

Jul. 25, 2014  (JP) ................. 2014-152346

(51) Int. Cl.
*G01C 3/08* (2006.01)
*G01N 21/64* (2006.01)
(Continued)

(52) U.S. Cl.
CPC ............. *G01N 21/64* (2013.01); *G02B 3/06* (2013.01); *G02B 21/0076* (2013.01);
(Continued)

(58) Field of Classification Search
CPC ............. G01N 21/64; G01N 21/6458; G01N 2021/6478; G01N 2201/06113; G02B 3/06; G02B 13/00; G02B 21/00; G02B 23/26

See application file for complete search history.

(56) References Cited

U.S. PATENT DOCUMENTS 5,442,413 A   8/1995  Tejima et al.
5,815,301 A   9/1998  Naiki et al.
(Continued)

FOREIGN PATENT DOCUMENTS

EP   2983027 A1    2/2016
JP   H06-265814 A  9/1994
(Continued)

OTHER PUBLICATIONS

International Search Report dated Oct. 13, 2015 issued in PCT/JP2015/070569.
(Continued)

*Primary Examiner* — Samantha K Abraham
(74) *Attorney, Agent, or Firm* — Scully Scott Murphy & Presser, P.C.

(57) ABSTRACT

The imaging optical system is for acquiring a clear final image, even if an intermediate image is formed at a position that overlaps with an optical device, by preventing scratches or the like of the optical device from becoming superimposed on the intermediate image, and has imaging lenses that form a final image and at least one intermediate image, a first phase-modulating element that imparts a spatial disturbance to a wavefront of light from an object, and a second phase-modulating element disposed at a position so that at least one intermediate image is interposed between the element and the element and that cancels the spatial disturbance, wherein the element has cylindrical lenses arranged with a space therebetween, and arranged so that a (Continued)

principal point of the whole system is positioned in a vicinity of a pupil position of the imaging lenses.

9 Claims, 9 Drawing Sheets

(51) Int. Cl.
*G02B 3/06* (2006.01)
*G02B 23/26* (2006.01)
*G02B 21/00* (2006.01)

(52) U.S. Cl.
CPC ......... *G02B 23/26* (2013.01); *G01N 21/6458* (2013.01); *G01N 2021/6478* (2013.01); *G01N 2201/06113* (2013.01)

(56) References Cited

U.S. PATENT DOCUMENTS

| | | | |
|---|---|---|---|
| 5,943,153 | A | 8/1999 | Naiki et al. |
| 6,738,195 | B2 | 5/2004 | Matsumoto et al. |
| 6,774,944 | B1 | 8/2004 | Fukuyama |
| 6,831,730 | B2 | 12/2004 | Matsumoto et al. |
| 6,842,280 | B2 | 1/2005 | Araki et al. |
| 8,482,637 | B2 | 7/2013 | Ohara et al. |
| 8,950,874 | B2 | 2/2015 | Tatsuno |
| 2003/0095342 | A1 | 5/2003 | Matsumoto et al. |
| 2004/0150879 | A1 | 8/2004 | Araki et al. |
| 2004/0160587 | A1 | 8/2004 | Matsumoto et al. |
| 2010/0110233 | A1 | 5/2010 | Ohara et al. |
| 2012/0063008 | A1 | 3/2012 | Jia et al. |
| 2013/0070217 | A1 | 3/2013 | Tatsuno |
| 2016/0025970 | A1 | 1/2016 | Fukuyama |

FOREIGN PATENT DOCUMENTS

| | | |
|---|---|---|
| JP | H08-292391 A | 11/1996 |
| JP | H10-257373 A | 9/1998 |
| JP | H11-109243 A | 4/1999 |
| JP | H11-211979 A | 8/1999 |
| JP | 2003-222795 A | 8/2003 |
| JP | 4011704 B2 | 11/2007 |
| JP | 2008-113860 A | 5/2008 |
| JP | 2008-245157 A | 10/2008 |
| JP | 2008-245266 A | 10/2008 |
| JP | 2008-268937 A | 11/2008 |
| JP | 2010-266813 A | 11/2010 |
| JP | 2013-083817 A | 5/2013 |
| WO | WO 2014/163114 A1 | 10/2014 |

OTHER PUBLICATIONS

International Search Report dated Oct. 13, 2015 issued in PCT/JP2015/070462.
International Search Report dated Oct. 20, 2015 issued in PCT/JP2015/070970.

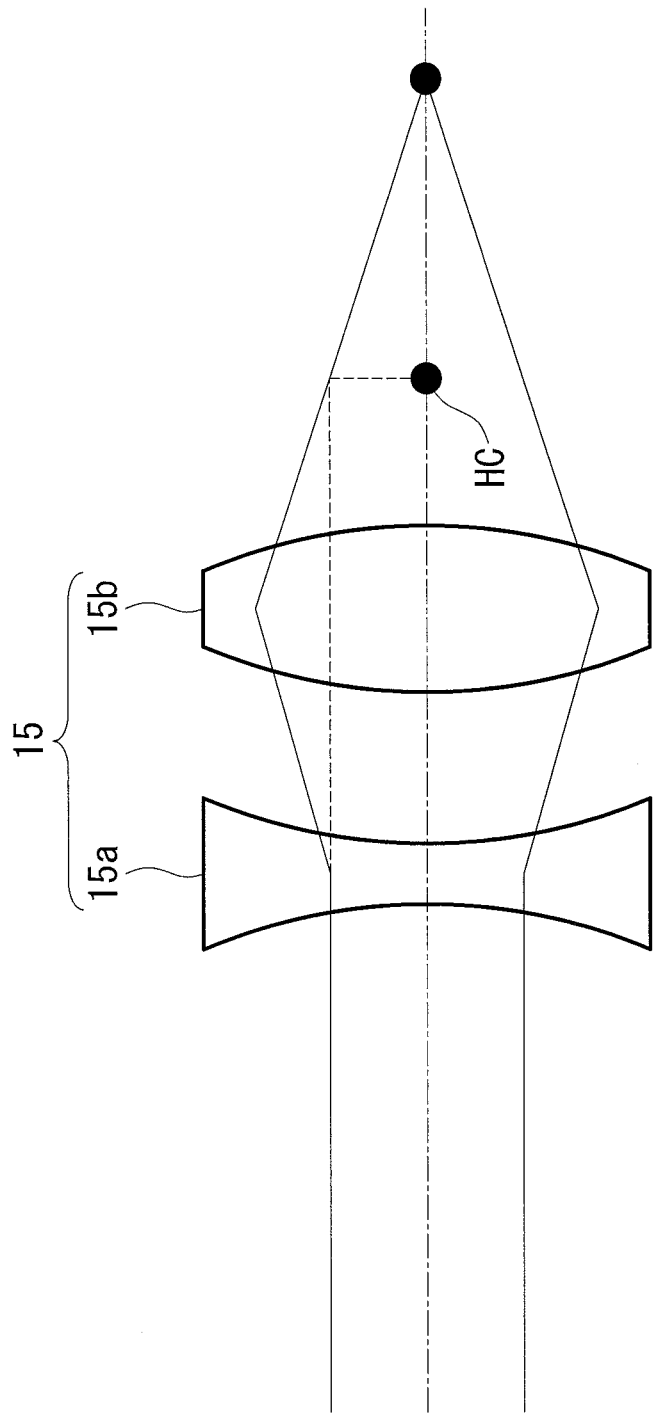

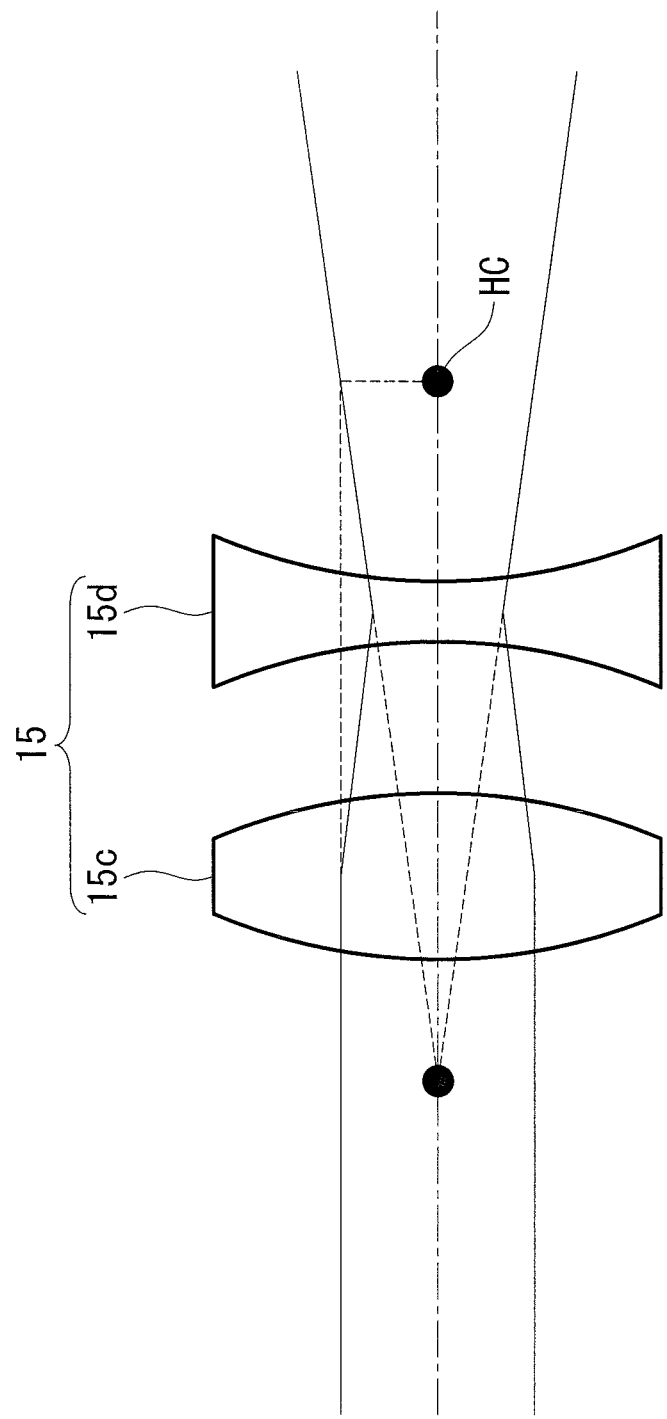

IMAGING OPTICAL SYSTEM, ILLUMINATION APPARATUS, OBSERVATION APPARATUS, AND WAVEFRONT RECOVERY DEVICE

CROSS-REFERENCE TO RELATED APPLICATIONS

This application is a Continuation Application of International Application No. PCT/JP2015/070569 filed on Jul. 17, 2015, which claims priority to Japanese Application No. 2014-152346 filed on Jul. 25, 2014. The contents of International Application No. PCT/JP2015/070569 and Japanese application No. 2014-152346 are incorporated herein by reference in its entirety.

TECHNICAL FIELD

The present invention relates to an imaging optical system, an illumination apparatus, an observation apparatus, and a wavefront recovery device.

BACKGROUND ART

In the related art, there is a known method in which the position of an in-focus point is moved in a direction parallel to an optical axis by adjusting the optical path length at an intermediate-image position (for example, see PTL 1).

CITATION LIST

Patent Literature

{PTL 1} Publication of Japanese Patent No. 4011704

SUMMARY OF INVENTION

An aspect of the present invention is imaging optical system comprising: a plurality of imaging lenses that form a final image and at least one intermediate image; a first phase-modulating element that is disposed closer to an object than any one of the intermediate images formed by the imaging lenses, and that imparts a spatial disturbance to a wavefront of light coming from the object; and a second phase-modulating element that is disposed at a position so that at least one of the intermediate images is positioned between the first phase-modulating element and the second phase-modulating element, and that cancels the spatial disturbance imparted to the wavefront of the light coming from the object by the first phase-modulating element, wherein at least one of the first phase-modulating element and the second phase-modulating element is provided with a plurality of cylindrical lenses that are arranged with a space therebetween in an optical-axis direction, and the plurality of cylindrical lenses are arranged so that a principal point of the whole system of the plurality of cylindrical lenses is positioned in a vicinity of a pupil position of the imaging lenses.

BRIEF DESCRIPTION OF DRAWINGS

FIG. 2 is a diagram showing an example phase-modulating element according to this embodiment provided in the observation apparatus in FIG. 1.

FIG. 5 is a diagram showing a modification of the phase-modulating element in FIG. 2.

DESCRIPTION OF EMBODIMENTS

An observation apparatus 1, an illumination apparatus 2, an imaging optical system 3, and a phase-modulating element 15 according to a first embodiment of the present invention will be described below with reference to the drawings.

Figure 1:
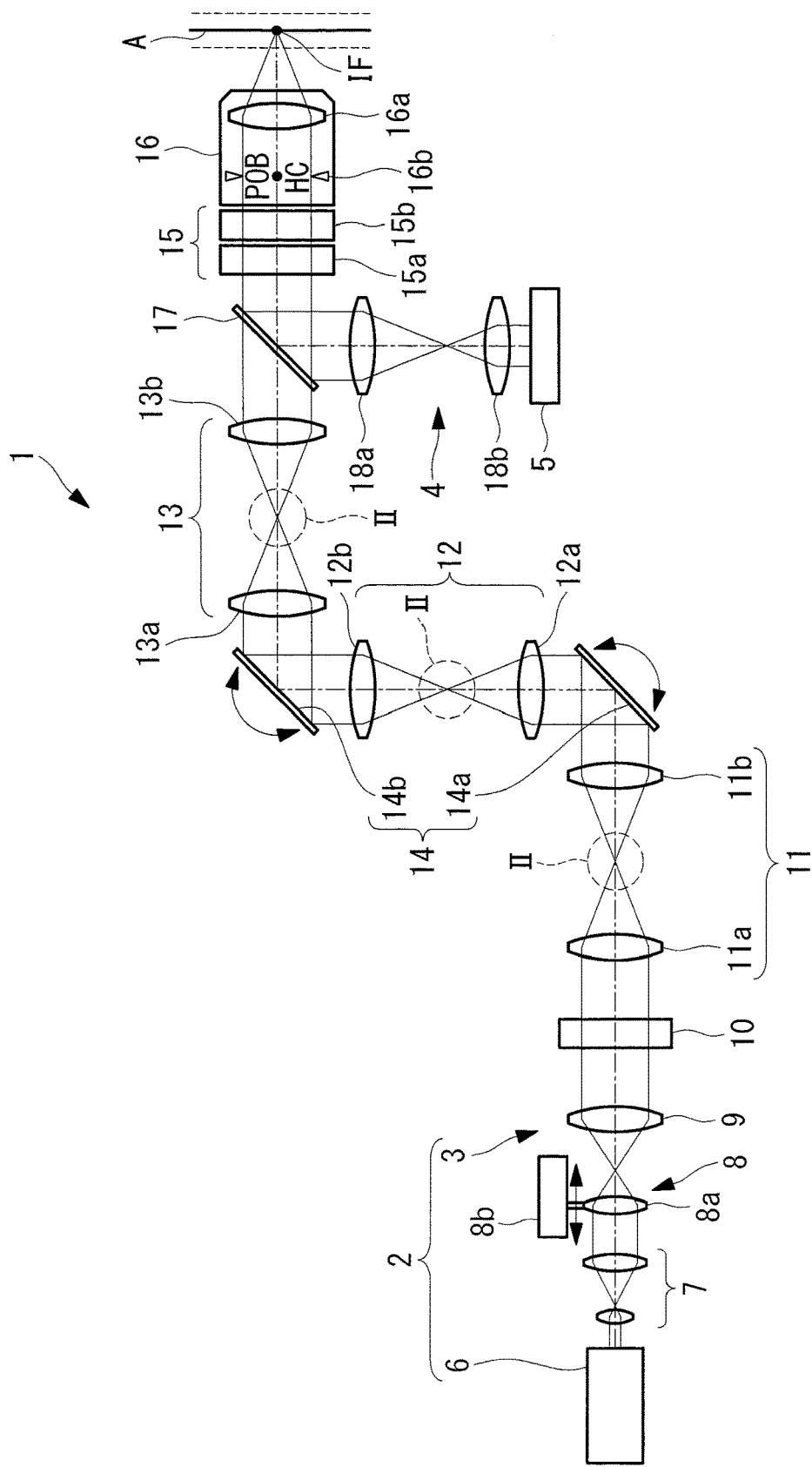
FIG. 1 is a diagram schematically showing the overall configuration of an observation apparatus according to a first embodiment of the present invention.

As shown in FIG. 1, the observation apparatus 1 according to this embodiment is, for example, a laser scanning multiphoton excitation microscope.

The observation apparatus 1 is provided with: an illumination apparatus 2 that radiates ultra-short pulsed laser light (hereinafter, simply referred to as laser light (illumination light)) onto an observation subject A; a detector optical system 4 that guides, to a photodetector, fluorescence emitted from the observation subject A due to the irradiation of the laser light by the illumination apparatus 2; and the photodetector 5 that detects the fluorescence guided thereto by the detector optical system 4.

The illumination apparatus 2 is provided with: a light source 6 that emits laser light; and an imaging optical system 3 that radiates the laser light coming from the light source 6 onto the observation subject A.

The imaging optical system 3 is provided with: a beam expander 7 that expands the beam diameter of the laser light coming from the light source 6; a Z-scanning portion 8 that forms an intermediate image by focusing the laser light that has passed through the beam expander 7 and that moves the position at which the intermediate image is formed in the optical-axis direction; and a collimating lens 9 that turns the laser light, which has formed the intermediate image after passing through the Z-scanning portion 8, into substantially collimated light.

In addition, the imaging optical system 3 is provided with: a first phase-modulating element (wavefront-disturbing element) 10 that is disposed at a position that allows the laser light, which has been turned into the substantially collimated light by the collimating lens 9, to pass therethrough; a plurality of relay lens pairs 11, 12, and 13 that relay the intermediate image formed by the Z-scanning portion 8; a scanner 14 that is constituted of two galvanometer mirrors 14a and 14b that are disposed among the relay lens pairs 11, 12, and 13; a second phase-modulating element (wavefront recovery device) 15 that is disposed at a position that allows the laser light, which has been turned into the substantially collimated light by passing through the relay lens pairs 11, 12, and 13, to pass therethrough; and an objective lens 16 that focuses the laser light that has passed through the second phase-modulating element 15 and irradiates the observation subject A therewith, and that also collects the fluorescence emitted from a light-focusing point of the laser light in the observation subject A.

The Z-scanning portion 8 is provided with: a focusing lens 8a that focuses the laser light whose beam diameter has been expanded by the beam expander 7; and an actuator 8b that moves the focusing lens 8a in the optical-axis direction. By moving the focusing lens 8a in the optical-axis direction by means of the actuator 8b, it is possible to move the position at which the intermediate image is formed in the optical-axis direction.

The first phase-modulating element 10 includes one or more cylindrical lenses formed of an optically transparent material. The first phase-modulating element 10 is configured so as to, when the laser light passes therethrough, impart, to the laser light, a wavefront spatial disturbance that changes in accordance with the surface shape of the first phase-modulating element in a one-dimensional direction orthogonal to the optical axis, thus causing astigmatism.

In addition, the first phase-modulating element 10 is disposed at a position that is optically conjugate with the pupil of the objective lens 16, described below, and to which the light is relayed by the relay lens pairs 11, 12, and 13, described below.

The relay lens pairs 11, 12, and 13 are configured so that the laser light that has been turned into substantially collimated light by the collimating lens 9 is focused by first lenses 11a, 12a, and 13a to form intermediate images II, and so that, subsequently, the spreaded laser light is collimated again by second lenses 11b, 12b, and 13b to restore substantially collimated light. In this embodiment, the three relay lens pairs 11, 12, and 13 are disposed in a direction parallel to the optical axis with spaces therebetween so that the intermediate images II are formed at three locations.

Each of the galvanometer mirrors 14a and 14b is provided so as to be pivotable about an axis orthogonal to the optical axis, and is configured so as to, by changing the pivoting angle thereof, impart an inclination angle to the reflected laser light. The axes of the two galvanometer mirrors 14a and 14b are arranged in a mutually twisted positional relationship so that the inclination angles of the laser light can be changed in two-dimensional directions. Each of the two galvanometer mirrors 14a and 14b is disposed at a position that is optically conjugate with the pupil of the objective lens 16, described later, and to which the light is relayed by the relay lens pairs 12 and 13.

The objective lens 16 is provided with: one or more lenses 16a that form a spot on the observation subject A by focusing the incident laser light; and an aperture stop 16b disposed at a pupil position.

The second phase-modulating element 15 according to this embodiment is formed of an optically transparent material, and is disposed at a position so that the three intermediate images II are positioned between the first phase-modulating element 10 and the second phase-modulating element 15. This second phase-modulating element 15 is configured so as to, by modulating the wavefront of the laser light that passes therethrough, cancel out the spatial disturbance of the wavefront, that is, astigmatism, that the first phase-modulating element 10 has imparted to the laser light.

In addition, the second phase-modulating element 15 according to this embodiment is provided with a cylindrical-lens group constituted of two cylindrical lenses 15a and 15b that are disposed with a space therebetween in the optical-axis direction. As shown in FIG. 2, the first cylindrical lens 15a has a negative power, the second cylindrical lens 15b has a positive power, and the powers of the cylindrical lenses 15a and 15b and the space between the cylindrical lenses 15a and 15b are set so that the power of the whole system of the cylindrical-lens group becomes positive.

By doing so, a principal point HC formed by the whole system of the second phase-modulating element 15 is disposed outside the second phase-modulating element 15 in the optical-axis direction. Also, in this embodiment, the second phase-modulating element 15 is disposed so that this principal point HC overlaps with the pupil position of the objective lens 16.

The detector optical system 4 is provided with: a dichroic mirror 17 that is disposed on the optical axis of the objective lens 16 and at the opposite side of the objective lens 16 relative to the second phase-modulating element 15; and two focusing lenses 18a and 18b that are disposed on the optical axis bent by the dichroic mirror 17. The dichroic mirror 17 has characteristics that allow laser light to pass therethrough and that reflect fluorescence, and is configured so as to deflect the fluorescence collected by the objective lens 16 by 90° to make the fluorescence enter the focusing lens 18a.

The photodetector 5 is, for example, a photomultiplier tube and is configured so as to detect the intensity of the incident fluorescence.

The operation of the thus-configured observation apparatus 1 according to this embodiment will be described below.

In order to observe the observation subject A by using the observation apparatus 1 according to this embodiment, the observation subject A is irradiated with the laser light emitted from the light source 6 of the illumination apparatus 2 by means of the imaging optical system 3. After the beam diameter thereof is expanded by the beam expander 7, the laser light passes through the Z-scanning portion 8, the collimating lens 9, and the first phase-modulating element 10.

The laser light is focused by the focusing lens 8a of the Z-scanning portion 8, and it is possible to adjust the light-focusing position thereof in the optical-axis direction by operating the actuator 8b.

In addition, by making the laser light pass through the first phase-modulating element 10, a spatial disturbance, that is, astigmatism is imparted to the wavefront thereof.

After the laser light passes through the first phase-modulating element 10, by making the laser light pass through the scanner 14 constituted of the three relay lens pairs 11, 12, and 13 and the two galvanometer mirrors 14a and 14b, the inclination angle of the beam bundle is changed, and the laser light passes through the dichroic mirror 17, while forming the intermediate images II. Then, the laser light passes through the second phase-modulating element 15 and is focused on the observation subject A by means of the objective lens 16.

With the laser light to which a spatial disturbance has been imparted to the wavefront thereof by the first phase-modulating element 10, even if the intermediate images II are formed by the relay lens pairs 11, 12, and 13, due to an astigmatic difference, point images thereof are expanded to a line-like shape, are expanded to an elliptical shape, or are expanded to a circular shape, thus forming obscure images. Then, the laser light is made to pass through the second phase-modulating element 15 before entering the objective lens 16, and thus, the spatial disturbance, that is, astigmatism, imparted to the wavefront by the first phase-modulating element 10, is canceled out. By doing so, a final image IF that is formed at the observation subject A by the objective lens 16 can be formed as a clear spot having a desired shape, for example, an airy-disk shape or a Gaussian beam shape.

In other words, because the intermediate images II are made obscure by the first phase-modulating element 10 and, additionally, the final image IF is made clear by the second phase-modulating element, even if some optical devices are disposed at the positions at which the intermediate images II are formed and scratches, foreign objects, defects, or the like exist at the surfaces or the interiors of such optical devices, it is possible to prevent image deterioration of the final image IF of the objective lens 16 caused by such scratches, foreign objects, defects, or the like of optical devices which are superimposed on the intermediate images II.

Figure 3A:
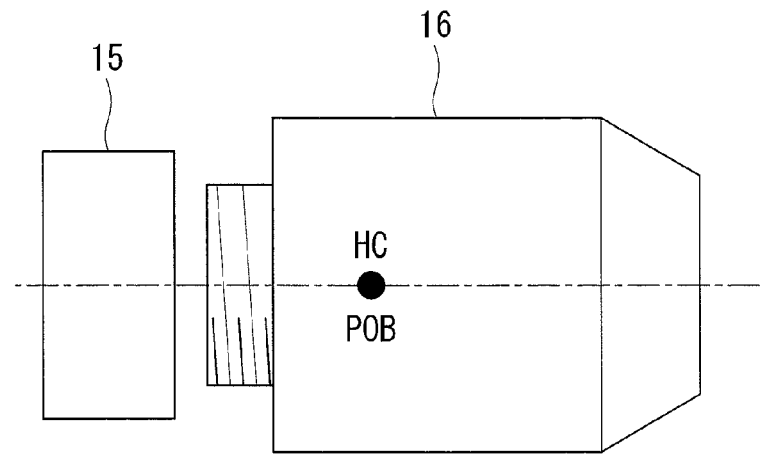
FIG. 3A is a diagram showing a state in which the phase-modulating element in FIG. 2 is disposed on the rear side of an objective lens of the observation apparatus in FIG. 1.
Figure 3B:
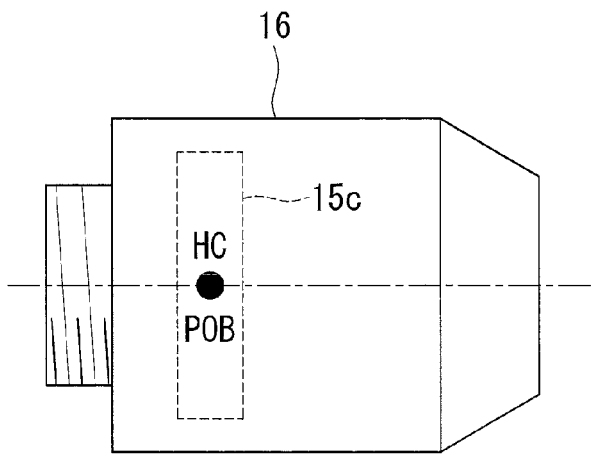
FIG. 3B is a diagram showing a state in which a phase-modulating element that is equivalent to the one in FIG. 3A is installed in the objective lens.

Also, with the second phase-modulating element 15 according to this embodiment, by appropriately setting the powers of the plurality of cylindrical lenses 15a and 15b and the space between the surfaces of the lenses 15a and 15b, it is possible to form a so-called retrofocus system in which the position of the principal point HC of the whole system of the second phase-modulating element 15 is positioned at the outside in the optical-axis direction. Therefore, as shown in FIG. 3A, by disposing the second phase-modulating element 15 outside the objective lens 16 in the optical-axis direction and making the principal point HC overlap with the pupil position POB of the objective lens 16, as shown in FIG. 3B, it is possible to achieve phase-modulation effects that are equivalent to the case in which a single cylindrical lens 15c having phase-modulation effects is disposed at the pupil position POB of the objective lens 16.

In other words, there is an advantage in that it is possible to equivalently dispose the second phase-modulating element 15c formed of a single cylindrical lens at the pupil position POB, which is positioned in the interior of the objective lens 16, merely by providing the second phase-modulating element 15, which is a retrofocus system, on the rear side of the objective lens 16 as an add-on component without modifying the objective lens 16. In many cases, only small spaces remain at the pupil position POB in the interior of the objective lens 16 due to the lens 16a, the aperture stop 16b, or the like that constitute the objective lens 16, and thus, it is difficult to install the phase-demodulating device 15 at the pupil position in reality. However, such a problem does not occur with this embodiment.

Also, the illumination apparatus 2 and the observation apparatus 1 according to this embodiment afford the following advantages by equivalently disposing the second phase-modulating element 15 at the pupil position POB of the objective lens 16.

Specifically, because the two galvanometer mirrors 14a and 14b and the first phase-modulating element 10 are disposed at the positions that are optically conjugate with the pupil position POB of the objective lens 16, as has been described above, the two galvanometer mirrors 14a and 14b and the first phase-modulating element 10 are also disposed at positions that are equivalently and optically conjugate with the second phase-modulating element 15.

Therefore, regardless of the changes made in the inclination angles of the galvanometer mirrors 14a and 14b, it is possible to make the laser light pass through the same region of the second phase-modulating element 15 that is equivalently disposed at the pupil position POB. By doing so, it is possible to impart the same phase-modulation effects to the laser light, and the conjugate relationship between the first phase-modulating element 10 and the second phase-modulating element 15 is also always maintained. As a result, it is possible to form a clear final image IF on the observation subject A by reliably canceling out the disturbance of the wavefront imparted by the first phase-modulating element 10 regardless of the inclination angles of the galvanometer mirrors. Accordingly, this embodiment can achieve an advantage in that it is possible to acquire a fluorescence image having a high spatial resolution.

Here, a method in which some optical parameters are given and thereby an astigmatic difference AS caused by the optical parameters is obtained will be described.

Figure 4A:
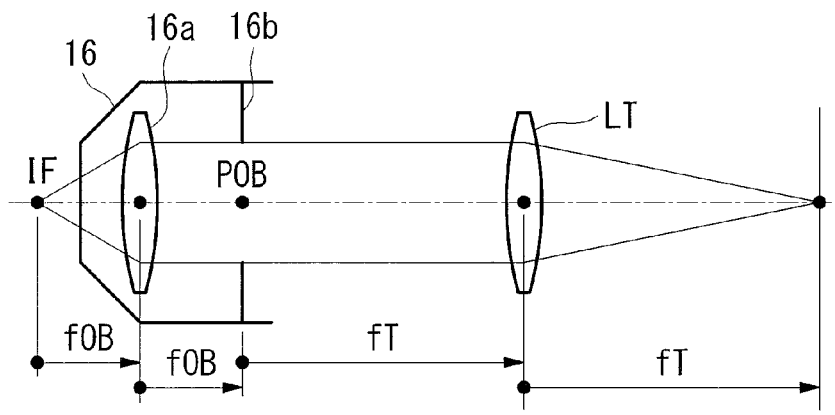
FIG. 4A is a diagram showing a basic optical system used for explaining a method of determining the astigmatic difference.
Figure 4B:
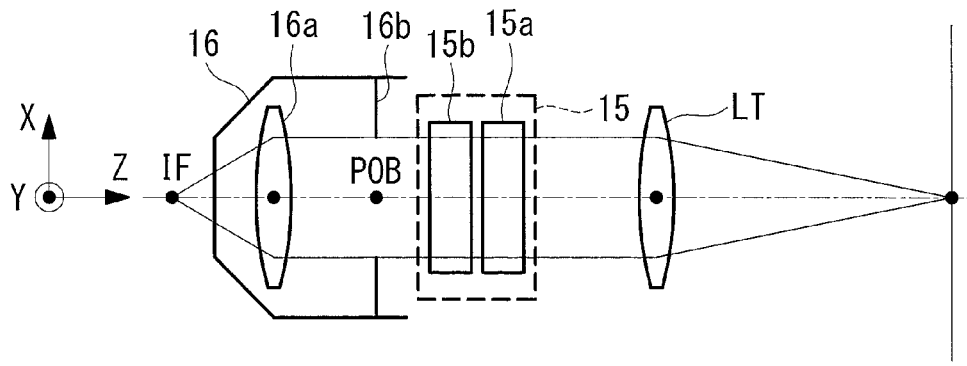
FIG. 4B is a diagram showing a plan view of a state in which a phase-modulating element used for explaining the method of determining the astigmatic difference is provided as an add-on component.
Figure 4C:
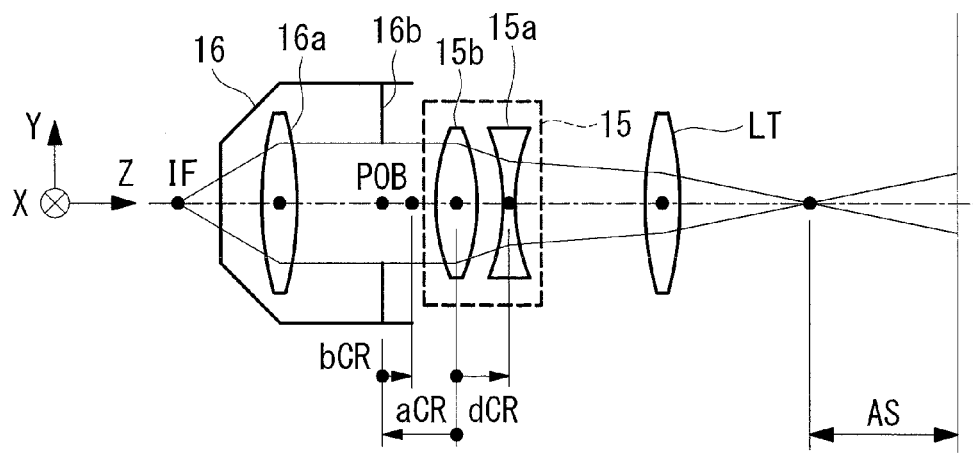
FIG. 4C is a diagram showing a side view of FIG. 4B.
Figure 4D:
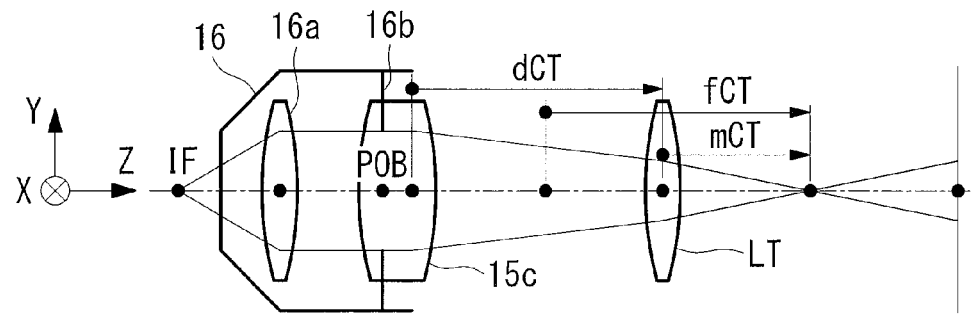
FIG. 4D is a diagram showing an optical system that is equivalent to the one in FIG. 4C.

It is possible to configure an optical system that is equivalent to a system in which the second phase-modulating element 15c constituted of a single cylindrical lens is disposed at the pupil position POB of the objective lens 16, as shown in FIG. 4D, by installing, as shown in FIGS. 4B and 4C, a retrofocus-system cylindrical-lens-type second phase-modulating element 15 in a basic optical system provided with an imaging lens LT and the objective lens 16 shown in FIG. 4A.

In the description using FIGS. 4A to 4D, for the sake of ease of understanding the phenomena, the final image IF is assumed to be a spot light source, and the direction in which light travels is taken as opposite to that of the laser light emitted from the laser source in FIG. 1. In addition, the sign of the distance between two points in the optical-axis direction is assumed to be based on the Z-axis, and the sign is assumed to be positive in the case in which the direction oriented toward the end point (indicated by an arrow) from the start point (indicated by black dot) of the distance between the two points is the same as the direction of the Z-axis shown in the figures.

The optical parameters that are set first are the focal distance fOB of the objective lens 16, the focal distance fT of the imaging lens LT, the distance aCR (<0) from the principal point of the positive-power cylindrical lens 15b of the retrofocus-system second phase-modulating element 15 to the front-side principal point of the whole system of the second phase-modulating element 15, the distance dCR between the principal points of the two cylindrical lenses 15a and 15b, and the combined focal distance fCR of the second phase-modulating element 15.

The combined focal distance fCR is expressed by the following general expression.

$$fCR = (fCR1 \cdot fCR2)/(fCR1 + fCR2 - dCR) \quad (1)$$

In the expression, fCR1 is the focal distance of the positive-power cylindrical lens 15b, and fCR2 is the focal distance of the negative-power cylindrical lens 15a.

In addition, aCR, which represents the position of the front-side principal point of the whole system of the second phase-modulating element 15, is expressed as the following expression.

$$aCR=(fCR1 \cdot dCR)/(fCR1+fCR2-dCR) \quad (2)$$

By simultaneously solving expressions (1) and (2), fCR1 and fCR2 are obtained.

In addition, the distance bCR between the front-side principal point and the rear-side principal point of the whole system is expressed as the following expression.

$$bCR=-dCR^2/(fCR1+fCR2-dCR) \quad (3)$$

Next, in FIG. 4D, the distance dCT between the rear-side principal point of the second phase-modulating element 15c, constituted of an equivalent single cylindrical lens, and the principal point of the imaging lens LT is expressed as the following expression.

$$dCT=fT-bCR \quad (4)$$

In addition, the combined focal distance fCT of the second phase-modulating element 15c, constituted of the equivalent single cylindrical lens, and the imaging lens LT is expressed by the following general expression.

$$fCT=(fCR \cdot fT)/(fCR+fT-dCT) \quad (5)$$

By assigning these values to the following expression (6), the rear-side focal position mCT is expressed as the following expression.

$$mCT=fT \cdot (fCR-dCT)/(fCR+fT-dCT) \quad (6)$$

Finally, by using the rear-side focal position mCT obtained by using expression (6), the astigmatic difference AS can be determined by the following expression.

$$AS=fT-mCT \quad (7)$$

Therefore, the optical parameters should be set so as to achieve a desired astigmatic difference AS.

In this embodiment, a device in which the powers of the cylindrical lenses 15a and 15b and the spacing of the cylindrical lenses 15a and 15b are set so that the power of the whole system becomes positive has been described as an example of the retrofocus-system second phase-modulating element 15. Alternatively, as shown in FIG. 5, a device in which the powers of the cylindrical lenses 15c and 15d and the spacing of the cylindrical lenses 15c and 15d are set so that the power of the whole system becomes negative may be employed.

In this case, as opposed to the second phase-modulating element shown in FIG. 2, which has the principal point HC at the cylindrical lens 15b having a positive power, the second phase-modulating element shown in FIG. 5 is different in that the principal point HC thereof is at the cylindrical lens 15d having a negative power.

Therefore, with the second phase-modulating element shown in FIG. 5, it is possible to make the above-described principal point HC overlap with the pupil position of the objective lens 16 by disposing the cylindrical lens 15d having a negative power so as to face the objective lens 16.

Figure 6A:
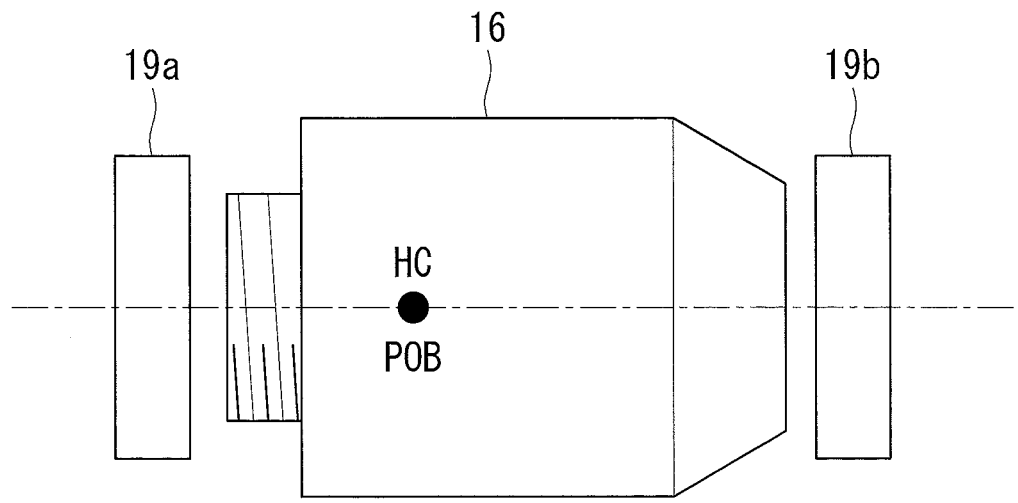
FIG. 6A is a diagram showing a state in which phase-modulating elements are disposed on either side of the objective lens of the observation apparatus in FIG. 1 at front and rear in the optical-axis direction thereof.
Figure 6B:
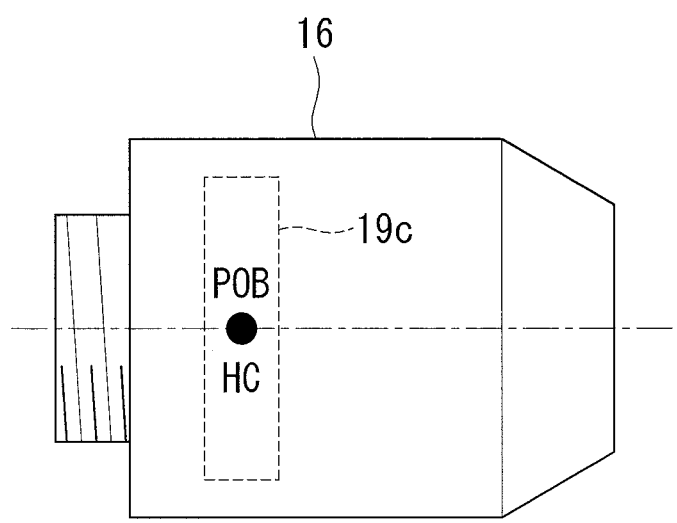
FIG. 6B is a diagram showing a state in which a phase-modulating element that is equivalent to the one in FIG. 6A is installed in the objective lens.

In this embodiment, the second phase-modulating element 15 that can be provided on the rear side of the objective lens 16 as an add-on component has been described as an example. Alternatively, as shown in FIG. 6A, it is permissible to employ a second phase-modulating element 19 that is constituted of two or more cylindrical lenses 19a and 19b that are disposed at the front and rear of the objective lens 16 at positions on either side of the objective lens 16. By doing so also, it is possible to make the principal point HC of the whole system of the second phase-modulating element 19 overlap with the pupil position POB of the objective lens 16. By doing so, as shown in FIG. 6B, it is possible to make the system equivalent to a system in which the second phase-modulating element 19c constituted of a single cylindrical lens is disposed at the pupil position POB.

In addition, instead of providing the add-on component on the rear side of the objective lens 16, the add-on component may be provided on the front side of the objective lens 16.

Figure 7:
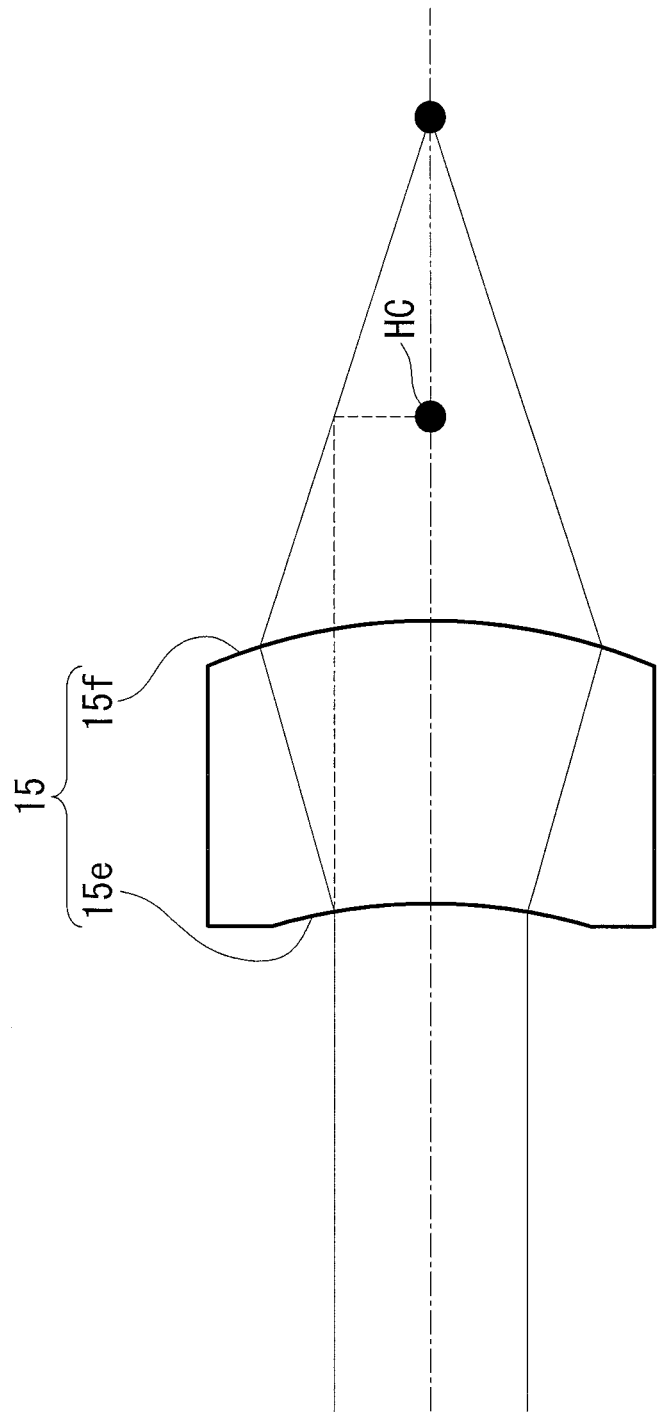
FIG. 7 is a diagram showing another modification of the phase-modulating element in FIG. 2.

In this embodiment, a device that is configured so that the power of the whole system becomes positive by using two cylindrical lenses 15a and 15b, as in FIG. 2, is employed as the second phase-modulating element 15. Alternatively, as shown in FIG. 7, by forming a surface 15e in one cylindrical lens as a concave surface, the surface 15e may be used instead of the cylindrical lens 15a, and, at the same time, by forming another surface 15f as a convex surface, the surface 15f may be used instead of the cylindrical lens 15b. By doing so, it is possible to make the power of the whole system positive, and it is also possible to dispose the principal point HC thereof outside the second phase-modulating element 15 in the optical-axis direction.

Figure 8:
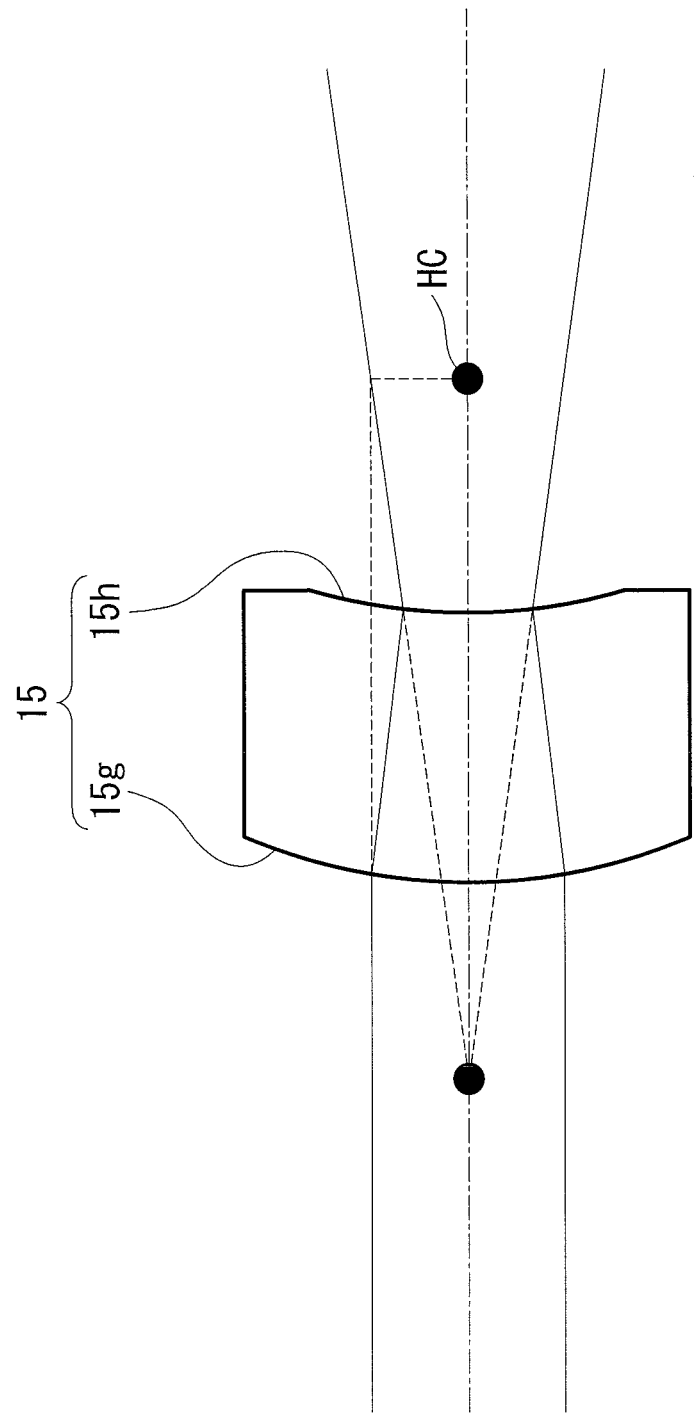
FIG. 8 is a diagram showing yet another modification of the phase-modulating element in FIG. 2.

Furthermore, as a modification of the above-described second phase-modulating element 15 shown in FIG. 7, it is possible to make the power of the whole system negative in a single cylindrical lens provided with a positive lens surface 15g and a negative lens surface 15h, as shown in FIG. 8, and it is also possible to dispose the principal point HC thereof outside the second phase-modulating element 15 in the optical-axis direction.

Next, an observation apparatus 20 according to a second embodiment of the present invention will be described with reference to the drawings.

Figure 9:
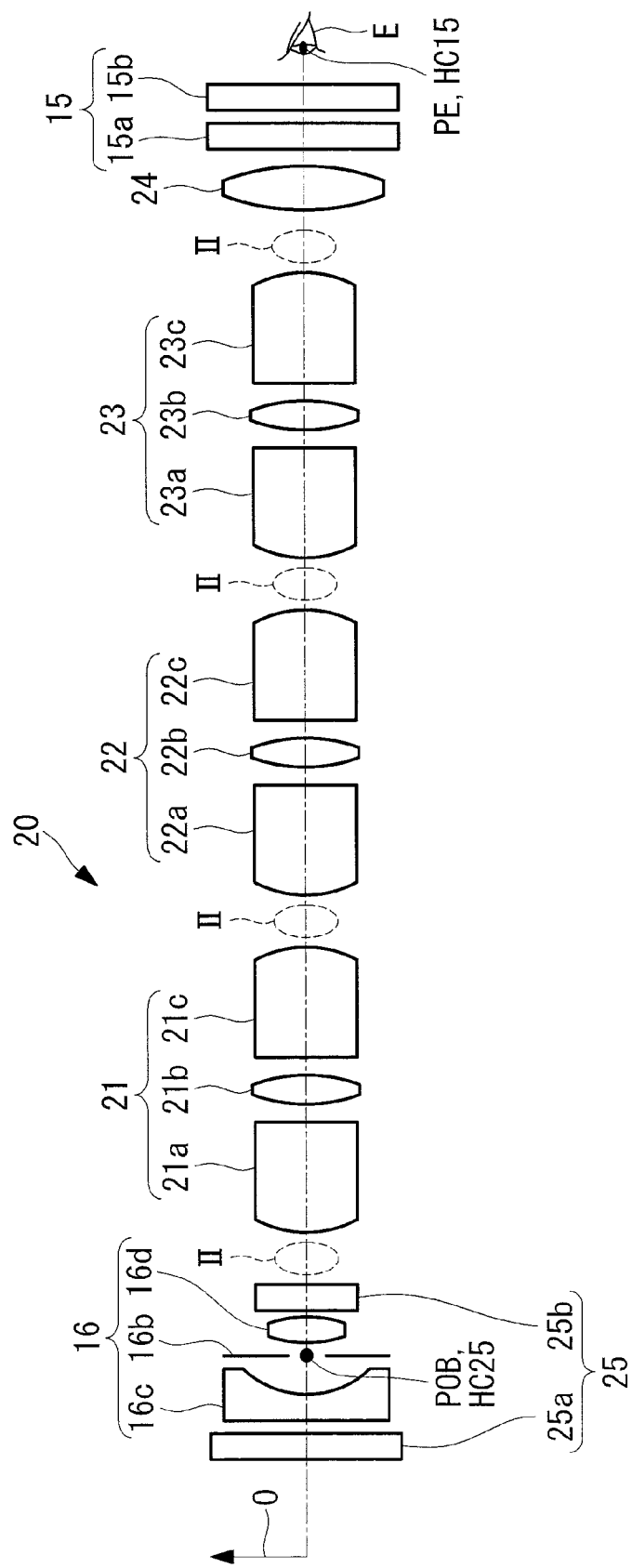
FIG. 9 is a diagram schematically showing the overall configuration of an observation apparatus according to a second embodiment of the present invention.

As shown in FIG. 9, the observation apparatus 20 according to this embodiment is, for example, a rigid endoscope.

The observation apparatus 20 is provided with: the objective lens 16; a first phase-modulating element 25; relay lens pairs 21, 22, and 23; an eyepiece lens 24, and the second phase-modulating element 15.

The first phase-modulating element 25 is provided with two or more cylindrical lenses 25a and 25b that are disposed at the front and rear of the objective lens 16 so that the objective lens 16 is positioned between the lenses 25a and 25b, in such a manner that a principal point HC25 of the whole system of the first phase-modulating element 25 overlaps with the pupil POB of the objective lens 15.

The objective lens 16 is provided with the aperture stop 16b and lenses 16c and 16d.

The relay lens 21 is provided with an imaging lens 21b and two field lenses 21a and 21c. The relay lens 22 is provided with an imaging lens 22b and two field lenses 22a and 22c. The relay lens 23 is provided with an imaging lens 23b and two field lenses 23a and 23c.

The second phase-modulating element 15 is provided with the two cylindrical lenses 15a and 15b, and a principal point HC15 formed by the whole system thereof is disposed so as to overlap with a pupil PE of an eye E.

The operation of the thus-configured observation apparatus 20 according to this embodiment will be described below.

Light emitted from an observation subject O is collected by the objective lens 16 and is also made to pass through the first phase-modulating element 25, and thus, a spatial disturbance, that is, astigmatism, is imparted to the wavefront thereof.

After passing through the first phase-modulating element 25, the light is made to pass through the relay lens pairs 21, 22, and 23, thus forming obscure intermediate images II. Furthermore, after passing through the eyepiece lens 24, this light is made to pass through the second phase-modulating element 15, thus canceling out the spatial disturbance, that is, astigmatism, of the wavefront. Therefore, on the retina (not shown) of the eye E, a clear final image is observed.

Specifically, because the intermediate images II are made obscure, even if scratches, foreign objects, defects, or the like exist in the vicinities of the intermediate images, for example, surfaces or interiors of the field lenses 21a, 21c, 22a, 22c, 23a, 23c or the like, it is possible to prevent such scratches, foreign objects, defects, or the like from deteriorating the final image.

Because this example does not include, for example, galvanometer mirrors, that is, a scanner, such as that in the first embodiment shown in FIG. 1, it is not necessarily required to make the principal point HC25 of the first phase-modulating element 25 completely overlap with the pupil surface POB of the objective lens 16, and it is sufficient that the principal point HC25 is positioned in the vicinity of the pupil surface POB. In addition, it is not necessarily required to make the principal point HC15 of the second phase-modulating element 15 completely overlap with the pupil surface PE of the eye E, and it is sufficient that the principal point HC15 is positioned in the vicinity of the pupil surface PE. Thus, in this case, it is sufficient that the above-described principal point HC25 and the above-described principal point HC15 are at optically conjugate positions.

As with the relationship between an object and an image in a general imaging optical system, which is relative and reversible, the wavefront-disturbing effect of the first phase-modulating element of the present invention and the wavefront-disturbance-canceling effect of the second phase-modulating element are also relative and reversible. In other words, in the optical system of the present invention, when the direction in which light travels is reversed, the roles of the first phase-modulating element and the second phase-modulating element are naturally switched. Therefore, the effects of the configurations based on the present invention are essentially invariable regardless of the direction with which light passing through the first phase-modulating element and the second phase-modulating element travels.

The inventor has arrived at the following aspects of the invention.

An aspect of the present invention is imaging optical system comprising: a plurality of imaging lenses that form a final image and at least one intermediate image; a first phase-modulating element that is disposed closer to an object than any one of the intermediate images formed by the imaging lenses, and that imparts a spatial disturbance to a wavefront of light coming from the object; and a second phase-modulating element that is disposed at a position so that at least one of the intermediate images is positioned between the first phase-modulating element and the second phase-modulating element, and that cancels the spatial disturbance imparted to the wavefront of the light coming from the object by the first phase-modulating element, wherein at least one of the first phase-modulating element and the second phase-modulating element is provided with a plurality of cylindrical lenses that are arranged with a space therebetween in an optical-axis direction, and the plurality of cylindrical lenses are arranged so that a principal point of the whole system of the plurality of cylindrical lenses is positioned in a vicinity of a pupil position of the imaging lenses.

With this aspect, the light that has been irradiated into the imaging lenses from the object side thereof forms a final image after being repeatedly focused, multiple times, by the imaging lenses. In this case, by passing through the first phase-modulating element that is disposed closer to the object than one of the intermediate images, a spatial disturbance is imparted to the wavefront of the light, and thus the formed intermediate images are made obscure. In addition, the light that has formed the intermediate images passes through the second phase-modulating element, thus canceling out the spatial disturbance imparted to the wavefront by the first phase-modulating element. By doing so, the final image formed after the second phase-modulating element is made clear.

In other words, even in the case in which the intermediate images are positioned in the vicinity of optical devices in which scratches, foreign objects, defects, or the like exist at the surfaces or the interiors thereof, by making the intermediate images obscure, it is possible to prevent the occurrence of a problem in which such scratches, foreign objects, defects, or the like become superimposed on the intermediate images, thus finally forming portions of a final image.

Also, by combining the plurality of cylindrical lenses by disposing the cylindrical lenses with a space therebetween in the optical-axis direction, it is possible to dispose the principal point of the whole system of the phase-modulating element at a position so that the principal point does not overlap with the cylindrical lenses. By doing so, even in the case in which there is no extra space in the vicinity of the pupil position of the imaging lenses, it is possible to achieve the same effects as the case in which a single phase-modulating element is disposed in the vicinity of the pupil position.

In particular, in an optical system having a scanner, in order to prevent the above-described problem in which scratches, foreign objects, defects, or the like that exist at the surfaces or the interiors of optical devices form portions of a final image, it is necessary to dispose the scanner, the pupil of the imaging lenses, the first phase-modulating element, and the second phase-modulating element in a conjugate manner. Even if the positions of the beam bundles are changed by the scanner when the above-described individual elements are set in a conjugate positional relationship, the beam bundles enter the second phase-modulating element at a certain position thereof, and thus it is possible to completely cancel out the spatial disturbance imparted to the wavefront by the first phase-modulating element.

In other words, in an optical system having a scanner, even in the case in which there is no extra space in the vicinity of the pupil position of the imaging lenses, by combining the plurality of cylindrical lenses by disposing the cylindrical lenses with a space therebetween in the optical-axis direction, it is possible to achieve the same effects as the case in which a single phase-modulating element is disposed so as to overlap with the pupil position.

In the above-described aspect, the sign of the power of at least one of the cylindrical lenses is opposite of the sign of the power of another cylindrical lens.

By doing so, by combining the negative-power cylindrical lens and the positive-power cylindrical lens, it is possible to easily set the position of the principal point of the whole system of the cylindrical-lens group, which serves as a phase-modulating element, outside the second phase-modulating element in the optical-axis direction. By doing so, the second phase-modulating element itself can be inserted at a position away from the pupil position of the imaging lenses in the optical-axis direction.

In the above-described aspect, the power of the whole system of the plurality of cylindrical lenses may be positive, and the power of the whole system of the plurality of cylindrical lenses may be negative.

In addition, another aspect of the present invention is an illumination apparatus provided with any one of the above-described imaging optical systems and a light source which is disposed at a position closer to an object than the imaging optical system and which generates illumination light to be irradiated into the imaging optical system.

With this aspect, by making the illumination light emitted from the light source disposed at the object side enter the imaging optical system, it is possible to irradiate the illumination light onto an illuminated subject disposed on the final-image side. In this case, because the intermediate images formed by the imaging optical system are made obscure by the first phase-modulating element, even if some optical devices are disposed at the intermediate-image positions and scratches, foreign objects, defects, or the like exist at the surfaces or the interiors of the optical devices, it is possible to prevent the occurrence of a problem in which such scratches, foreign objects, defects, or the like become superimposed on the intermediate images, thus finally forming portions of a final image.

In addition, another aspect of the present invention is an observation apparatus provided with any one of the above-described imaging optical systems and a photodetector which detects light from an observation subject disposed at a final-image position of the imaging optical system.

With this aspect, the above-described observation subject is irradiated with a light spot that serves as a clear final image that is formed by preventing images of scratches, foreign objects, defects, or the like that exist at the surfaces or the interiors of the optical devices from becoming superimposed on the intermediate images, and thus it is possible to detect light emitted from the observation subject by using the photodetector.

In addition, another aspect of the present invention is an observation apparatus provided with: any one of the above-described imaging optical systems; a light source that is disposed on a position closer to an object than the imaging optical system and that emits illumination light that enters the imaging optical system; a scanner that scans the illumination light coming from the light source; and a photodetector that detects light emitted from an observation subject disposed at a final-image position of the imaging optical system.

With this aspect, the illumination light emitted from the light source disposed on the object side is made to enter the imaging optical system and passes through the scanner in the process of traveling therethrough while forming the intermediate images, and thus the illumination light is scanned on the observation subject disposed at the final-image position. Then, light emitted from the individual scanning positions of the observation subject by being irradiated with the illumination light is detected by the photodetector, and thus, it is possible to generate an image of the observation subject on the basis of the scanning positions of the illumination light and the light-intensity information detected by the detector. In this case, because a light spot that serves as a clear final image is formed on the observation subject by preventing images of scratches, foreign objects, defects, or the like at the surfaces or the interiors of the optical devices from becoming superimposed on the intermediate images, it is possible to acquire a clear image of the observation subject.

In the above-described aspect, the light source may be a laser light source, and the photodetector may be provided with a confocal pinhole and a photoelectric conversion device.

By doing so, it is possible to observe an observation subject by using a clear confocal image in which images of scratches, foreign objects, defects, or the like at the intermediate-image positions do not appear.

In addition, another aspect of the present invention is an observation apparatus provided with any one of the above-described imaging optical systems, wherein the light source is an ultra-short pulsed laser light source.

With this aspect, multiphoton fluorescence emitted by irradiating an observation subject disposed at the final-image position with ultra-short pulsed illumination light emitted from the light source disposed on the object side is detected by the photodetector, it is possible to generate an image of the observation subject. In this case, because a light spot that serves as a clear final image is formed on the observation subject by preventing images of scratches, foreign objects, defects, or the like at the surface or the interior of the optical devices from becoming superimposed on the intermediate images, it is possible to acquire a clear multiphoton-fluorescence image of the observation subject.

In addition, another aspect of the present invention is a wavefront recovery device to be used in an imaging optical system,
    wherein the imaging optical system comprises:
        a plurality of imaging lenses that form a final image and at least one intermediate image; and
        a wavefront-disturbing element that is disposed closer to an object than any one of the intermediate images formed by the imaging lenses, and that imparts a spatial disturbance to a wavefront of light coming from the object,
    wherein the wavefront recovery device is disposed at a position on an optical path so that at least one of the intermediate images is positioned between the wavefront-disturbing element and the wavefront recovery device, and is configured to cancel the spatial disturbance imparted to the wavefront of the light coming from the object by the wavefront-disturbing element, wherein the wavefront recovery device is provided with a plurality of cylindrical lenses disposed with a space therebetween in an optical-axis direction so that a principal point of the whole system of the plurality of cylindrical lenses is positioned at the pupil position of the imaging lenses or in the vicinity of a pupil position of the imaging lenses.

With this aspect, merely by inserting the wavefront recovery device according to this aspect at a position of an optical path, which is different from the pupil position of the imaging lenses, it is possible to achieve the same effects as the case in which a single wavefront recovery device is disposed at the pupil position or in the vicinity of the pupil position. Therefore, by employing the wavefront recovery device according to this aspect in the case in which there is a small insertion space in the vicinity of the pupil position because the system is very small, as with an objective lens of an endoscope, or in the case in which an existing imaging lens, such as a microscope objective-lens unit, is used, it is possible to perform illumination or observation in which images without scratches, foreign objects, defects, or the like existing at intermediate-image positions.

The aforementioned aspects afford an advantage in that, even if an intermediate image is formed at a position overlapping with an optical device, it is possible to acquire a clear final image by preventing scratches, foreign objects, defects, or the like of the optical device from becoming superimposed on the intermediate image.

REFERENCE SIGNS LIST

HC, HC15, HC25 principal point of cylindrical lens
IF final image

II intermediate image
POB pupil position
1 observation apparatus
2 illumination apparatus
3 imaging optical system
5 photodetector
6 light source
10, 25 first phase-modulating element (wavefront-disturbing element)
11, 12, 13 relay lens pair (imaging lens)
14 scanner
15 second phase-modulating element (wavefront recovery device)
15a, 15b, 15c, 15d cylindrical lens
16 objective lens (imaging lens)
20 observation apparatus
21, 22, 23 relay lens pair (imaging lens and field lens)
24 eyepiece lens

The invention claimed is:

1. An imaging optical system comprising:
a plurality of imaging lenses that form a final image and at least one intermediate image;
a first phase-modulating element that is disposed closer to an object than any one of the intermediate images formed by the imaging lenses, and that imparts a spatial disturbance to a wavefront of light coming from the object; and
a second phase-modulating element that is disposed at a position so that at least one of the intermediate images is positioned between the first phase-modulating element and the second phase-modulating element, and that cancels the spatial disturbance imparted to the wavefront of the light coming from the object by the first phase-modulating element,
wherein at least one of the first phase-modulating element and the second phase-modulating element is provided with a plurality of cylindrical lenses that are arranged with a space therebetween in an optical-axis direction, and the plurality of cylindrical lenses are arranged so that a principal point of. the whole system of the plurality of cylindrical lenses is positioned in a vicinity of a pupil position of the imaging lenses.

2. The imaging optical system according to claim 1, wherein the sign of the power of at least one of the cylindrical lenses is opposite of the sign of the power of another cylindrical lens.

3. The imaging optical system according to claim 2, wherein the power of the whole system of the plurality of cylindrical lenses is positive.

4. The imaging optical system according to claim 2, wherein the power of the whole system of the plurality of cylindrical lenses is negative.

5. An illumination apparatus comprising:
an imaging optical system according to claim 1; and
a light source which is disposed at a position closer to an object than the imaging optical system and which generates illumination light to be irradiated into the imaging optical system.

6. An observation apparatus comprising:
an illumination apparatus according to claim 5; and
a photodetector which detects light from an observation subject disposed at a final-image position of the imaging optical system.

7. The observation apparatus according to claim 6, further comprising:
a scanner that scans the illumination light coming from the light source.

8. The observation apparatus according to claim 7, wherein the light source is an ultra-short pulsed laser light source.

9. A wavefront recovery device to be used in an imaging optical system,
wherein the imaging optical system comprises:
a plurality of imaging lenses that form a final image and at least one intermediate image; and
a wavefront-disturbing element that is disposed closer to an object than any one of the intermediate images formed by the imaging lenses, and that imparts a spatial disturbance to a wavefront of light coming from the object,
wherein the wavefront recovery device is disposed at a position on an optical path so that at least one of the intermediate images is positioned between the wavefront-disturbing element and the wavefront recovery device, and is configured to cancel the spatial disturbance imparted to the wavefront of the light coming from the object by the wavefront-disturbing element,
wherein the wavefront recovery device is provided with a plurality of cylindrical lenses arranged with a space therebetween in an optical-axis direction so that a principal point of the whole system of the plurality of cylindrical lenses is positioned in a vicinity of a pupil position of the imaging lenses.

* * * * *